(12) United States Patent
Tang

(10) Patent No.: US 9,019,491 B2
(45) Date of Patent: Apr. 28, 2015

(54) METHOD AND APPARATUS FOR MEASURING SHAPE AND THICKNESS VARIATION OF A WAFER

(75) Inventor: Shouhong Tang, Santa Clara, CA (US)

(73) Assignee: KLA—Tencor Corporation, Milpitas, CA (US)

(*) Notice: Subject to any disclaimer, the term of this patent is extended or adjusted under 35 U.S.C. 154(b) by 301 days.

(21) Appl. No.: 13/525,858

(22) Filed: Jun. 18, 2012

(65) Prior Publication Data

US 2013/0188179 A1 Jul. 25, 2013

Related U.S. Application Data

(60) Provisional application No. 61/588,561, filed on Jan. 19, 2012.

(51) Int. Cl.
*G01N 21/00* (2006.01)
*G01B 11/25* (2006.01)
*G01B 11/30* (2006.01)

(52) U.S. Cl.
CPC ............ *G01B 11/254* (2013.01); *G01B 11/306* (2013.01)

(58) Field of Classification Search
CPC ............. G01B 11/254; G01B 11/2527; G01B 11/306; G01N 21/9501
USPC .............................. 356/237.1–237.6, 605, 618
See application file for complete search history.

(56) References Cited

U.S. PATENT DOCUMENTS

| | | | |
|---|---|---|---|
| 5,307,152 A * | 4/1994 | Boehnlein et al. ............ | 356/605 |
| 5,621,529 A | 4/1997 | Gordon et al. | |
| 5,750,986 A * | 5/1998 | Genovese ..................... | 250/235 |
| 5,995,226 A | 11/1999 | Abe et al. | |
| 6,731,391 B1 * | 5/2004 | Kao et al. ...................... | 356/605 |
| 6,847,458 B2 | 1/2005 | Freischlad et al. | |
| 6,999,183 B2 * | 2/2006 | Nielsen et al. ................ | 356/612 |
| 7,812,942 B2 | 10/2010 | Moulin et al. | |
| 2011/0128371 A1 | 6/2011 | Gastaldo et al. | |

* cited by examiner

*Primary Examiner* — Michael A Lyons
*Assistant Examiner* — Shawn Decenzo
(74) *Attorney, Agent, or Firm* — Suiter Swantz pc llo

(57) ABSTRACT

The invention provides a new dual-sided Moiré wafer analysis system that integrates wafer flatness measurement capability with wafer surface defect detection capability. The invention may be, but is not necessarily, embodied in methods and systems for simultaneously applying phase shifting reflective Moiré wafer analysis to the front and back sides of a silicon wafer and comparing or combining the front and back side height maps. This allows wafer surface height for each side of the wafer, thickness variation map, surface nanotopography, shape, flatness, and edge map to be determined with a dual-sided fringe acquisition process. The invention also improves the dynamic range of wafer analysis to measure wafers with large bows and extends the measurement area closer to the wafer edge.

23 Claims, 4 Drawing Sheets

METHOD AND APPARATUS FOR MEASURING SHAPE AND THICKNESS VARIATION OF A WAFER

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled METHOD AND APPARATUS FOR MEASURING SHAPE AND THICKNESS VARIATION OF A WAFER BY PHASE REFLECTIVE MOIRE TECHNOLOGY, naming Shouhong Tang as an inventor, filed Jan. 19, 2012, Application Ser. No. 61/588,561.

TECHNICAL FIELD

The present invention relates generally to silicon chip integrated circuit manufacture and, more particularly, to a technique for creating thickness variation maps and detecting defects in silicon wafers using phase shifting reflective Moiré wafer analysis applied to both sides of the wafer.

BACKGROUND

Silicon wafers used to manufacture Integrated circuit chips inevitably include some defects that can result in errors in the integrated circuits when etched onto the wafers. Different types of defects can occur at different locations in the wafer. For example, surface adhesions where pieces of the top layer of the wafer have been pulled away from the body of the wafer typically occur on the front or back face of the wafer. Edge defects occur around the perimeter of the wafer. Slip line cracks typically occur along crystal lattice lines. Detecting of all of these different types of defects has proved to be a challenging task.

Prior silicon wafer defect detection technologies have not adequately addressed the challenges of determining thickness variations in silicon wafers and detecting the different types of defects that occur in the wafers used to manufacture integrated circuit chips. This results in the inefficient fabrication of defective chips. There is, therefore, a need for more effective methods and systems for detecting various types of defects in silicon wafers prior to etching the integrated circuits onto the wafers.

SUMMARY

The invention meets the needs described above in a new dual-sided Moiré fringe acquisition system that integrates wafer flatness measurement capability with wafer surface defect detection capability. The invention may be, but is not necessarily, embodied in methods and systems for applying phase shifting reflective Moiré wafer analysis to the front and back sides of a wafer simultaneously. The system compares or combines the front and back side height maps to generate a thickness variation map for the wafer. This allows wafer surface height for each side of the wafer, thickness variation map, surface nonotopography, shape, flatness, and edge map to be determined with a dual-sided fringe acquisition process. The invention also improves the dynamic range of wafer analysis to measure wafers with large bows and extends the measurement area closer to the wafer edge.

The invention is specifically designed for, but is not limited to, systems for analyzing silicon wafers used to manufacture integrated circuits. Accordingly, the invention may be practiced through methods and systems for determining thickness variation maps for silicon wafers and using this information for detecting defects in the wafers. A Moiré pattern is projected across a first side of the wafer in multiple fringe acquisition iterations, with each iteration being projected across the first side of the wafer at a different angle. Multiple fringe patterns are acquired for the first side of the wafer from the multiple fringe acquisition iterations. Multiple slope maps are computed by phase shifting the fringe patterns. The multiple slope maps are then integrated to construct a height map for the first side of the wafer.

The procedure described above is repeated for the second side of the wafer to create a height map for the second side of the wafer. These procedures may be, but need not be, performed simultaneously for both sides of the wafer. A thickness variation map is then generated from the height maps for the first and second sides of the wafer. The surface nanotopography may then be determined from the first and second side height maps. A thickness variation map may also be computed from the first and second side height maps and the flatness, edge map and other parameters of the wafer can may be determined from one or more of the height maps and/or the thickness variation map.

The system may include two screens, each for projecting the Moiré patterns onto respective sides of the wafer. Alternatively, a single screen may be employed along with two mirrors that each reflect the same Moiré patterns onto respective sides of the wafer. The system is effective for detecting adhesion defects, slip line defects, and edge defects in the analyzed wafers.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the invention may be better understood with reference to the accompanying figures in which.

DETAILED DESCRIPTION OF ILLUSTRATIVE EMBODIMENTS

Figure 1:
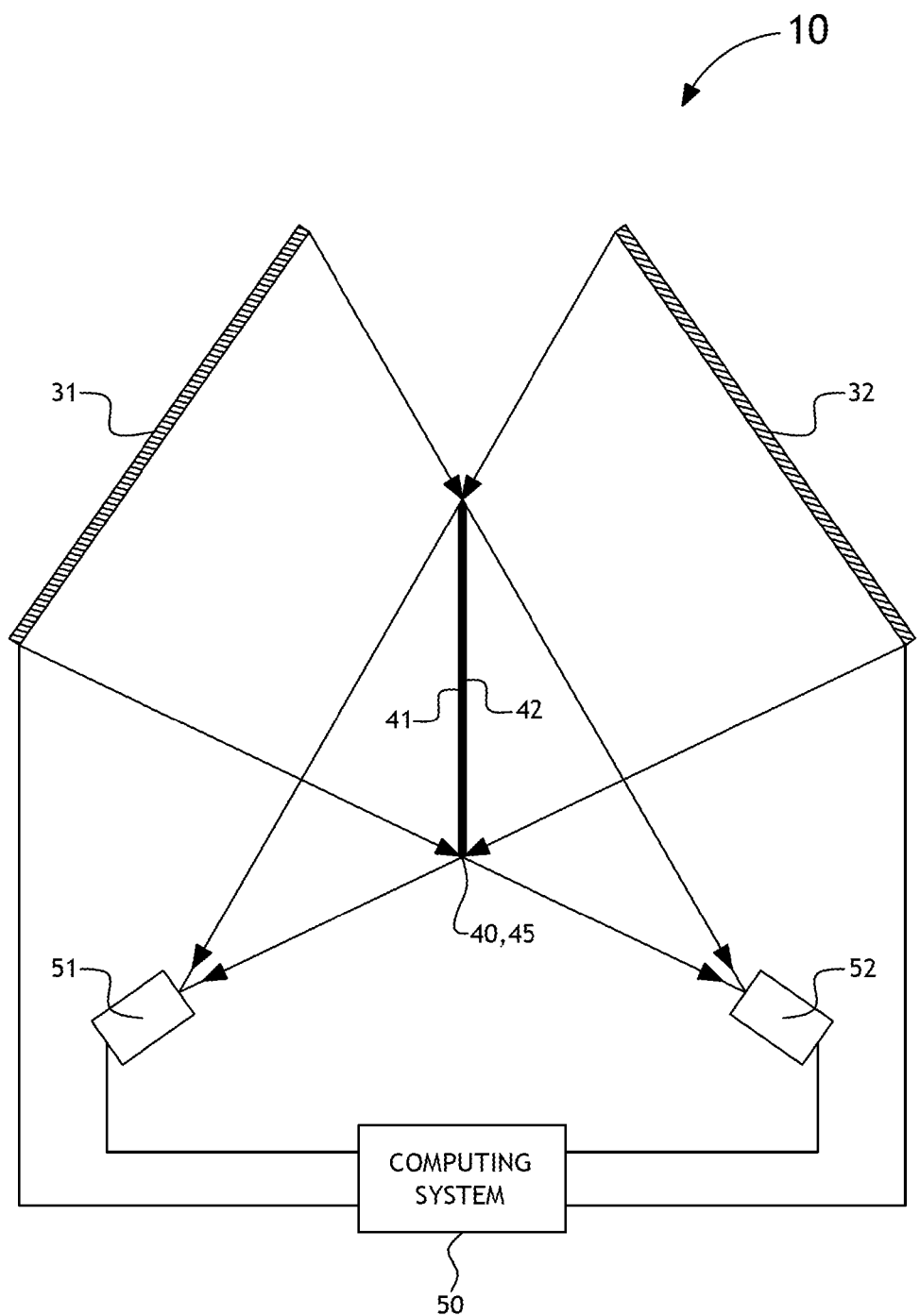
FIG. 1 is a conceptual illustration of a dual-screen example of the dual-sided Moiré wafer analysis system.

The illustrative embodiments of the invention provide methods and system for dual-sided Moiré wafer analysis for generation thickness variation maps and detecting defects in silicon wafers used to manufacturer integrated circuit chips. The disclosure provides, but is not limited to, two specific examples of dual-sided Moiré wafer analysis systems. A first example of the system employs two screens, each projecting the Moiré patterns onto a respective side of the wafer. A second example of the system employs a single screen and two mirrors that each reflect the same Moiré patterns onto a respective side of the wafer. The system is effective for detecting adhesion defects, slip line defects; and edge defects in the analyzed wafers. The dual-sided Moiré wafer analysis system may, but need not necessarily, obtain the surface slope maps for both sides of the wafer simultaneously. Simultaneous wafer analysis may be preferred to enhance the speed of the process and accommodate dedicated hardware data processing in the host computer system.

The dual-sided Moiré wafer analysis systems take advantage of the fact that the surface height maps used to determine wafer thickness variation can be measured by integrating two or more surface slope maps obtained by phase shifting reflective Moiré technology. The surface nanotopography may then be determined from the first and second side height maps. A thickness variation map may also be computed from the first and second side height maps and the flatness, edge map and other parameters of the wafer can may be determined from one or more of the height maps and/or the thickness variation map.

Prior defect detection techniques include temporal phase shifting interferometric technology as described in U.S. Pat. No. 6,847,458, which is incorporated by reference. This technique combines two phase-shifting Fizeau interferometers to simultaneously obtain two single-sided distance maps between each side of a wafer and corresponding reference flats, and compute thickness variation and shape of the wafer from these data and a calibrated distance map between two reference flats. The resulting system is able to measure the surface height on both sides of the wafer simultaneously to determine thickness variations of the wafer rapidly and accurately.

However, the phase shifting interferometric technique is sensitive to vibration, acoustic noises, and air turbulence that corrupt the phase of interferograms differently at different times. This results in degradation of the wafer dimension computations even though the measurement data utilizes multiple phase-shifted interferograms to compute the wafer dimensions. The distortion sources can vary over time and change unpredictably making it difficult to maintain calibration of the system.

Phase shifting reflective Moiré wafer analysis has also been utilized to detect wafer defects, as described in U.S. Pat. No. 7,812,942, which is also incorporated by reference. This technique is effective for detecting surface defects, such as slip line defects on a silicon wafer. However, this technology is applied to only a single side of the wafer. As a result, front or back side surface height maps, thickness variation map, wafer shape, and wafer flatness are not available with this technique.

In comparison to prior interferometric technology, the present dual-sided Moiré wafer analysis systems exhibit faster throughput for macro defect detection, lower cost, less sensitivity to vibration and air turbulence, and a larger dynamic range providing the ability to measure a wafer with a large bow and to measure surface area closer to the wafer edge. The phase shifting reflective Moiré technology is less sensitive to the vibration, acoustic noise, and air turbulence than the interferometric technology.

In comparison to prior single-sided Moiré technology, the present dual-sided Moiré system provides the advantages of measuring the front and back side surface height, preferably simultaneously, which allows determination of thickness variation map, the surface nanotopography, flatness, and edge map of the wafer in addition to providing all of the surface defect detection functionality of the single-sided Moiré wafer analysis systems.

Referring now to FIG. 1, a dual-screen example system 10 for implementing dual-sided Moiré wafer analysis may be used to simultaneously acquire fringe patterns for the front side 41 and the back side 42 of a silicon wafer 40 positioned in a wafer support 45 of the system. A first screen 31 projects an alternating pattern of continuous light and dark bands (Moiré pattern) onto the front side 41 of the wafer 40. The Moiré pattern typically includes at least three fringe transitions between light and dark bands. A first detector 51 records a fringe pattern from the reflected Moiré pattern and communicates the front side fringe pattern to a host computer system 50 for analysis. Similarly, a second screen 32 projects a Moiré pattern across the back side 42 of the wafer 40. A second detector 52 records a fringe pattern from the reflected Moiré pattern and communicates the back side fringe pattern to the host computer system 50 for analysis. The detectors may be CCD, CMOS, TD cameras or any other suitable type of detector currently existing or developed in the future.

The Moiré pattern may be projected across each side of the wafer at several different rotational angles to obtain multiple slope maps, which are integrated together to create a surface height map for each side of the wafer. Projecting the Moiré pattern at different angles is useful for detecting linear defects, such as slip line cracks, at different angels on the wafer. Multiple projections at different angles are also useful for constructing a complete edge map for the wafer. The surface height map for each side is typically computed by integrating at least two different derivative slope maps obtained from Moiré pattern projections at different angles across the surface of the wafer. The slope map may be computed directly from the fringe patterns acquired for the associated projection by phase shifting the resulting fringe pattern. The height maps are used to generate a thickness variation map for the wafer. The surface nanotopography may then be determined from the first and second side height maps. A thickness variation map may also be computed from the first and second side height maps and the flatness, edge map and other parameters of the wafer can may be determined from one or more of the height maps and/or the thickness variation map. Defects, such as surface adhesions, slip line defects, and edge can then be identified from the measured and computed information.

Figure 2:
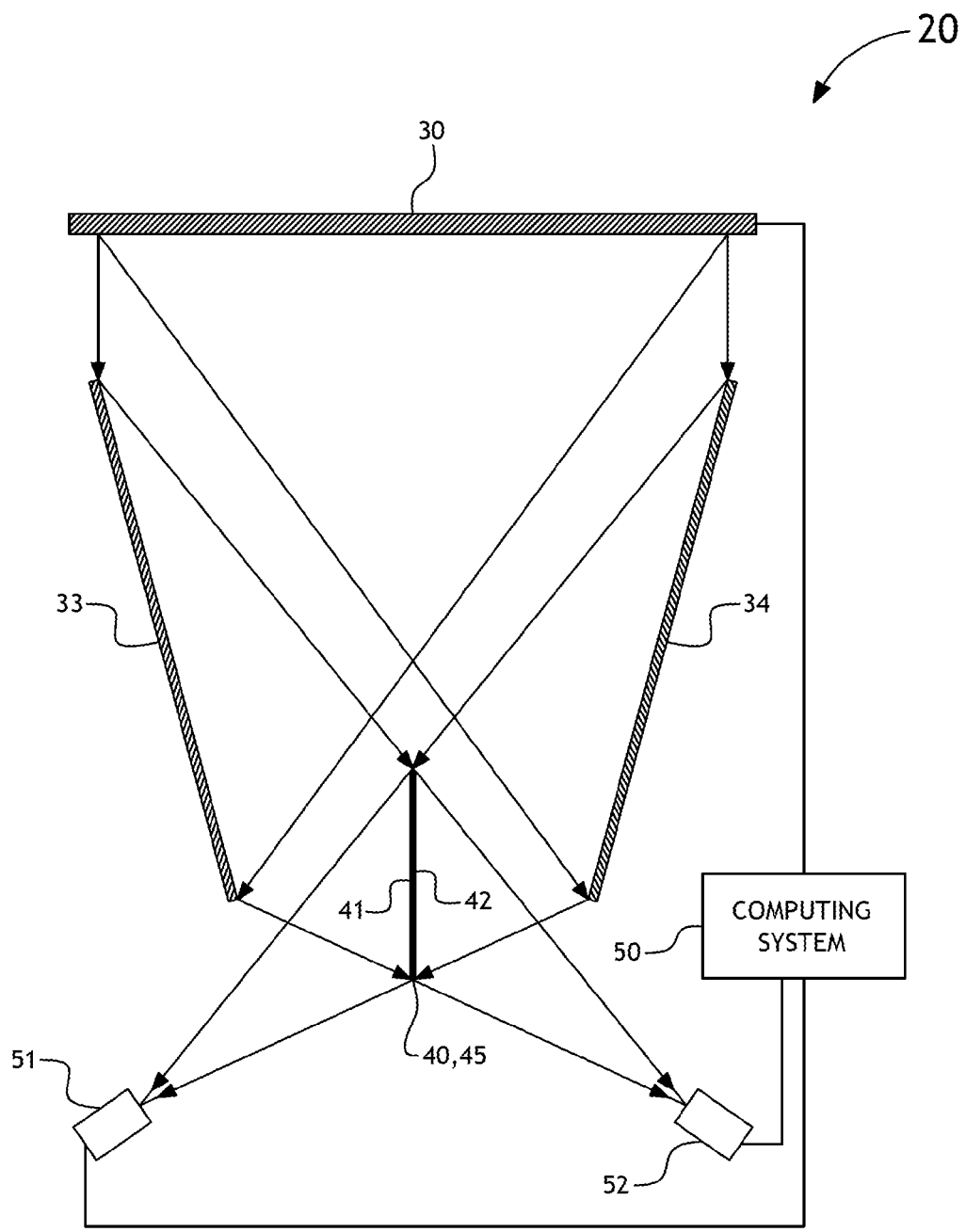
FIG. 2 is a conceptual illustration of a single-screen example of the dual-sided Moiré wafer analysis system.

A single-screen example system 20 for implementing dual-sided Moiré wafer analysis is shown in FIG. 2. This system is similar to the dual-screen system 10 shown in FIG. 1, except that the same Moiré pattern projected by a single screen 30 is projected across both sides of the wafer. The Moiré pattern from the screen 30 is projected onto mirrors 33 and 34, which each reflect the pattern onto a respective side of the wafer 40, an shown in FIG. 2. The single screen example system in FIG. 2 provides a system that has more measurement sensitivity than the dual-screen system in FIG. 1 because the single screen alternative provides longer optical path from the screen 30 to the wafer 40 within a similar physical dimensions of the system. The measurement sensitivity can be an important parameter for a defect detection system.

Figure 3:
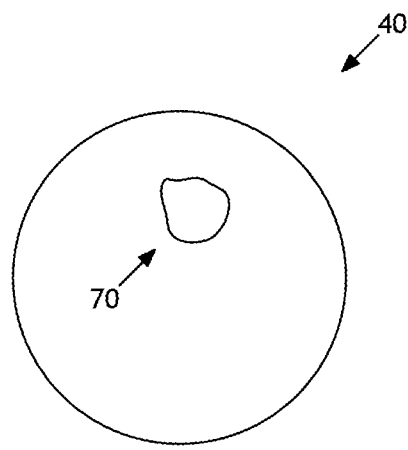
FIG. 3 is a conceptual illustration of an adhesion defect that can be detected by the dual-sided Moiré wafer analysis system.
Figure 4:
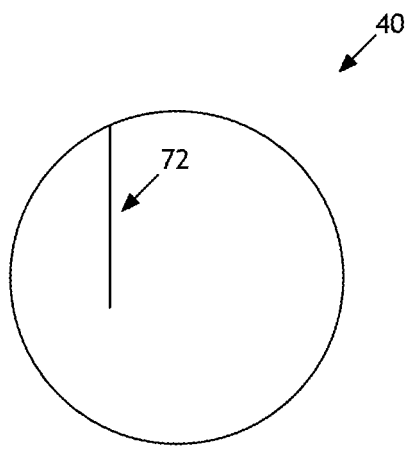
FIG. 4 is a conceptual illustration of a slip line defect that can be detected by the dual-sided Moiré wafer analysis system.

FIGS. 3-4 are highly diagrammatic pictorial illustrations of typical defect types detected by the dual-sided Moiré wafer analysis systems. Those skilled in the art will understand that wafers are typically formed on a millimeter scale whereas defects generally appear on a nanometer scale. It will be therefore be appreciated that the defects pictured are highly exaggerated and may be simplified for illustrative convenience. In addition, other types of defects, such as bumps, pits, dents, scratches, flatness variation, etc. can also be detected. The defect types illustrated in FIGS. 3-4 are therefore merely provided as conceptual examples that do not imply limitations on the capabilities to the systems.

FIG. 3 is a conceptual illustration of an adhesion defect 70 on the wafer 40 that can be detected by the dual-sided Moiré wafer analysis systems. This type of defect typically occurs when a piece of the surface of the wafer is pulled away from the body of the wafer. The dual-sided Moiré wafer analysis systems are effective at detecting adhesion defects because this type of defect shows up as a thickness variation obtained by comparing the front and back side surface height maps for the wafer.

FIG. 4 is a conceptual illustration of a slip line defect 72 that can be detected by the dual-sided Moiré wafer analysis systems. This type of crack defect typically occurs along a lattice line in the crystal forming the wafer. The dual-sided Moiré wafer analysis systems are effective at detecting slip line defects because multiple Moiré patterns are projected at different angles across each side of the wafer. While a first fringe pattern may not pick up a slip line that is perpendicular to the Moiré pattern projection direction, a second Moiré pattern is projected at a different angle will pick up the missed slip line. Since the lattice lines in the crystal are known, at least two projections, each at an angle to the known lattice lines, are generally effective at detecting slip line defects occurring along the known lattice lines.

Figure 5:
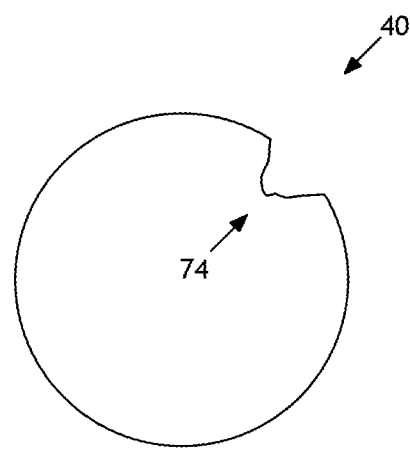
FIG. 5 is a conceptual illustration of an edge defect that can be detected by the dual-sided Moiré wafer analysis system.

FIG. 5 is a conceptual illustration of an edge defect 74 that can be detected by the dual-sided Moiré wafer analysis systems. While interferometric technology is generally ineffective for edge defect detection, the present system has a greater dynamic range of wafer defect wafer analysis to measure wafers with large bows and extends the measurement area closer to the wafer edge. Multiple Moiré pattern projections at different angles can be integrated together to produce an accurate edge map to pick up the edge defects on the wafer. Additional Moiré patterns may be projected at additional angles to increase the resolution of the height maps in order to detect flatness defects and small nanotopographic defects, such as surface bumps and pits, and fill out the edge image of the wafer.

Figure 6:
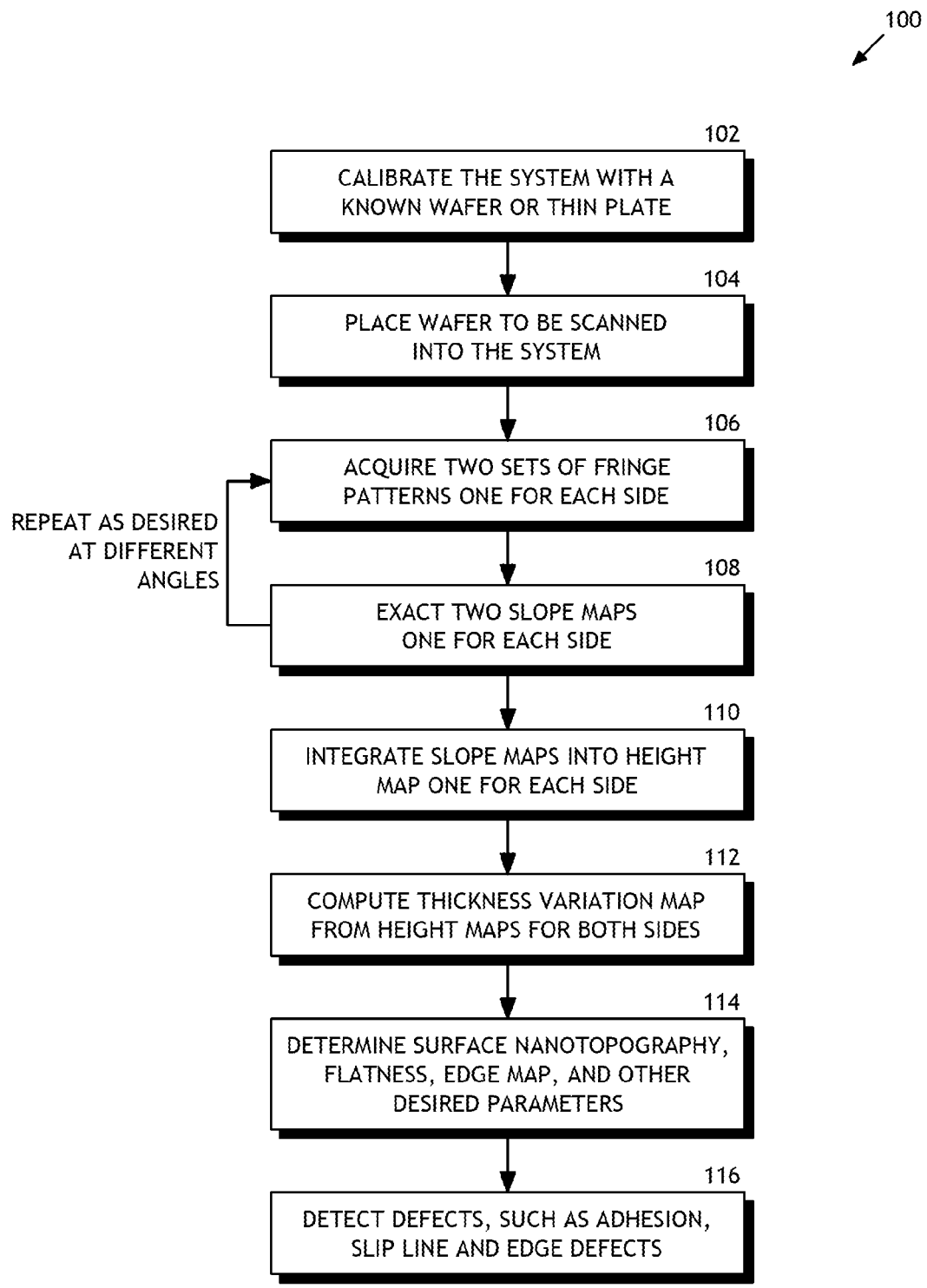
FIG. 6 is a logic flow diagram for operating the dual-sided Moiré wafer analysis system.

FIG. 6 is a logic flow diagram 100 for the dual-sided Moiré wafer analysis systems. The method for measuring the shape and thickness variation of the wafer begins in step 102 with calibration of the system characteristics using a known flat wafer or thin plate. Step 102 is followed by step 104, in which a wafer to be analyzed is placed into the dual-sided Moiré wafer analysis system. Step 104 is followed by step 106, in which two sets of fringe patterns, each including at least three phase shifting fringe transitions, are obtained, one for each side of the wafer. Step 106 is followed by step 108, in which two slope maps are computed from these two sets of intensity maps, one for each side of the wafer. The system may then loop through steps 106 and 108, as desired, to obtain additional sets of fringe pattern intensity maps for the wafer at a different rotational angles with respect to the wafer. At least two fringe acquisition iterations at different angles are typically conducted and additional fringe acquisition iterations may be conducted at different rotational angles to improve the measurement quality. Two slope maps, one for each side of the wafer, are computed from the fringe pattern intensity maps for each iteration.

Step 108 is followed by step 110, in which the slope maps for the respective sides of the wafer are integrated to create a height map for each side of the wafer. Step 110 is followed by step 112, in which a thickness variation map for the wafer may be computed from the height maps. For example, "A" may be considered to represent the height map for the front side and "B" may be considered to represent the height map for the backside of a wafer. The wafer shape is determined as (A+B)/2, the wafer thickness is determined as A−B. The nanotopography of the first side of the wafer is the highpass map of A, and the nanotopography of the second side of the wafer is the highpass map of B. Step 112 is followed by step 114, in which other desired information, such as the surface nanotopography, wafer flatness, edge map and other parameters may be computed from one or more of the thickness variation map and/or the height maps for the front and back sides of the wafer. Step 114 is followed by step 116, in which various types of defects, such as adhesion, slip line and edge defects are identified from this data.

It should be noted that some defects can be detected directly from the slope maps obtained in step 108. In order to determine the size of a defect quantitatively, such as the bump height, the slope maps obtained directly from the system are integrated to the surface height maps. In lithography, it is very importance to know the front surface height variation after the wafer is chucked down, or the back surface is forced to be flat, such as the PV, the peak and valley, within a die area. The surface height variation and defects on both sides of a wafer result in the PV changes. Thus the thickness variation map becomes very important. The thickness variation map is not only used to detect defects but also used for the quantitative measurement.

It is contemplated herein that the present invention may consist (but not required to consist) of adapting or reconfiguring presently existing systems. Alternatively, original equipment may be provided embodying the invention.

The computer system may include, but is not limited to, a personal computer system, mainframe computer system, workstation, image computer system, parallel processor, or any other device known in the art. In general, the term "computer system" may be broadly defined to encompass any device having one or more processors, which execute instructions from a memory medium.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

It is further contemplated that each of the embodiments of the method described above may include any other step(s) of any other method(s) described herein. In addition, each of the embodiments of the method described above may be performed by any of the systems described herein.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. A dual-sided Moiré wafer analysis system, comprising:
a wafer support operable for positioning a silicon wafer to be analyzed;
a first screen configured to project a Moiré pattern from the first screen toward a first side of the wafer in multiple fringe acquisition iterations, wherein each fringe acquisition iteration comprises projecting the Moiré pattern across the first side of the wafer from a different rotational angle with respect to the first side of the wafer;
a first detector for acquiring multiple fringe patterns for the first side of the wafer, each fringe pattern reflected from the first side of the wafer during a corresponding fringe acquisition iteration of the first side of the wafer;
a computer system operable for computing multiple slope maps for the first side of the wafer, each slope map for the first side of the wafer computed based on a corresponding fringe pattern for the first side of the wafer;
wherein the computer system is further operable for integrating the multiple slope maps for the first side of the wafer to construct a height map for the first side of the wafer;
a second screen configured to project a Moiré pattern from the second screen toward a second side of the wafer in multiple fringe acquisition iterations, wherein each fringe acquisition iteration comprises projecting the Moiré pattern across the second side of the wafer from a different rotational angle with respect to the second side of the wafer;
a second detector for recording multiple fringe patterns for the second side of the wafer, each fringe pattern reflected from the second side of the wafer during a corresponding fringe acquisition iteration of the second side of the wafer;
wherein the computer system is further operable for computing multiple slope maps for the second side of the wafer, each slope map for the second side of the wafer computed based on a corresponding fringe pattern for the second side of the wafer;

wherein the computer system is further operable for integrating the multiple slope maps for the second side of the wafer to construct a height map for the second side of the wafer; and wherein the computer system is further operable for creating a thickness variation map for the wafer from the height maps for the first and second sides of the wafer.

2. The dual-sided Moiré wafer analysis system of claim 1, wherein the computer system is further operable for computing each slope maps by phase shifting a corresponding fringe pattern.

3. The dual-sided Moiré wafer analysis system of claim 1, wherein corresponding Moiré pattern are projected across the first and second sides of the wafer simultaneously.

4. The dual-sided Moiré wafer analysis system of claim 1, wherein computer system is further operable for computing surface nanotopography, flatness, and edge map for the wafer.

5. The dual-sided Moiré wafer analysis system of claim 1, wherein the computer system is further operable for detecting a defect in the wafer from one or more of the first side height map, the second side height map, and the thickness variation map for the wafer.

6. The dual-sided Moiré wafer analysis system of claim 5, wherein the defect comprises an adhesion defect.

7. The dual-sided Moiré wafer analysis system of claim 5, wherein the defect comprises a slip line defect.

8. The dual-sided Moiré wafer analysis system of claim 5, wherein the defect comprises an edge defect.

9. A dual-sided Moiré wafer analysis system, comprising:
a wafer support operable for positioning a silicon wafer to be analyzed;
a screen configured to project a Moiré pattern in multiple fringe acquisition iterations, wherein each fringe acquisition iteration corresponds to a different rotational angle between the projected Moiré pattern and the wafer;
a first mirror for reflecting the fringe acquisition iterations across a first side of the wafer;
a first detector for acquiring multiple fringe patterns for the first side of the wafer, each fringe pattern reflected from the first side of the wafer during a corresponding fringe acquisition iteration of the first side of the wafer;
a computer system operable for computing multiple slope maps for the first side of the wafer, each slope map for the first side of the wafer computed based on a corresponding fringe pattern for the first side of the wafer;
wherein the computer system is further operable for integrating the multiple slope maps for the first side of the wafer to construct a height map for the first side of the wafer;
a second mirror for reflecting the fringe acquisition iterations across a second side of the wafer;
a second detector for acquiring multiple fringe patterns for the second side of the wafer, each fringe pattern reflected from the second side of the wafer during a corresponding fringe acquisition iteration of the second side of the wafer;
wherein the computer system is further operable for computing multiple slope maps for the second side of the wafer, each slope map for the second side of the wafer computed based on a corresponding fringe pattern for the second side of the wafer;

wherein the computer system is further operable for integrating the multiple slope maps for the second side of the wafer to construct a height map for the second side of the wafer; and wherein the computer system is further operable for creating a thickness variation map for the wafer from the height maps for the first and second sides of the wafer.

10. The dual-sided Moiré wafer analysis system of claim 9, wherein the computer system is further operable for computing each slope maps by phase shifting a corresponding fringe pattern.

11. The dual-sided Moiré wafer analysis system of claim 9, wherein corresponding Moiré patterns are projected across the first and second sides of the wafer simultaneously.

12. The dual-sided Moiré wafer analysis system of claim 9, wherein the computer system is further operable for computing surface nanotopography, flatness, and edge map for the wafer.

13. The dual-sided Moiré wafer analysis system of claim 9, wherein the computer system is further operable for detecting a defect in the wafer from one or more of the first side height map, the second side height map, and the thickness variation map for the wafer.

14. The dual-sided Moiré wafer analysis system of claim 13, wherein the defect comprises an adhesion defect.

15. The dual-sided Moiré wafer analysis system of claim 13, wherein the defect comprises a slip line defect.

16. The dual-sided Moiré wafer analysis system of claim 13, wherein the defect comprises a edge defect.

17. A method for detecting defects in a wafer, comprising the steps of:
projecting a Moiré pattern across a first side of the wafer in multiple fringe acquisition iterations, wherein each fringe acquisition iteration comprises projecting the Moiré pattern across the first side of the wafer from a different rotational angle with respect to the first side of the wafer;
acquiring multiple fringe patterns for the first side of the wafer, each fringe pattern reflected from the first side of the wafer during a corresponding fringe acquisition iteration of the first side of the wafer;
computing multiple slope maps for the first side of the wafer, each slope map for the first side of the wafer computed based on a corresponding fringe pattern for the first side of the wafer;
integrating the multiple slope maps for the first side of the wafer to construct a height map for the first side of the wafer;
projecting a Moiré pattern across a second side of the wafer in multiple fringe acquisition iterations, wherein each fringe acquisition iteration comprises projecting the Moiré pattern across the second side of the wafer from a different rotational angle with respect to the second side of the wafer;
acquiring multiple fringe patterns for the second side of the wafer, each fringe pattern reflected from the second side of the wafer during a corresponding fringe acquisition iteration of the second side of the wafer;
computing multiple slope maps for the second side of the wafer, each slope map for the second side of the wafer computed based on a corresponding fringe pattern for the second side of the wafer;
integrating the multiple slope maps for the second side of the wafer to construct a height map for the second side of the wafer;

computing first and second side surface height maps, surface nanotopography, flatness and thickness variation of the wafer; and computing a thickness variation map for the wafer from the first and second side surface height maps.

18. The method of claim 17, further comprising the steps of:

reflecting the Moiré pattern with a first mirror from a screen onto the first side of the wafer; and reflecting the Moiré pattern with a second mirror from the screen onto the second side of the wafer.

19. The method of claim 17, further comprising the step of determining surface nanotopography, flatness, and edge map for the wafer.

20. The method of claim 17, further comprising the step of detecting a defect in the wafer from one or more of the first side height map, the second side height map, and the thickness map for the wafer.

21. The method of claim 17, wherein the defect comprises an adhesion defect.

22. The method of claim 17, wherein the defect comprises a slip line defect.

23. The method of claim 17, wherein the defect comprises an edge defect.

* * * * *